US009944303B2

United States Patent
Sabo et al.

(10) Patent No.: US 9,944,303 B2
(45) Date of Patent: Apr. 17, 2018

(54) EQUIPMENT TROLLEY

(71) Applicant: Karl Storz SE & Co. KG, Tuttlingen (DE)

(72) Inventors: Alexander Sabo, Tuttlingen (DE); Andreas Jansche, Zimmern ob Rottweil (DE); Anika Guempel, Bodmann-Ludwigshafen (DE); Wolfgang Mueller-Beiter, Sigmaringendorf (DE); Rainer Schairer, Albstadt (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 0 days.

(21) Appl. No.: 14/625,194

(22) Filed: Feb. 18, 2015

(65) Prior Publication Data

US 2015/0259004 A1   Sep. 17, 2015

(30) Foreign Application Priority Data

Feb. 18, 2014 (DE) .................. 10 2014 101 999

(51) Int. Cl.
| | |
|---|---|
| B62D 3/00 | (2006.01) |
| B62B 3/04 | (2006.01) |
| B62B 3/02 | (2006.01) |
| A61B 50/10 | (2016.01) |
| A61B 50/13 | (2016.01) |
| A47B 57/40 | (2006.01) |

(Continued)

(52) U.S. Cl.
CPC ............. B62B 3/04 (2013.01); A61B 50/10 (2016.02); A61B 50/13 (2016.02); B62B 3/02 (2013.01); A47B 57/408 (2013.01); A47B 2031/003 (2013.01); A47B 2031/006 (2013.01); F16M 13/02 (2013.01)

(58) Field of Classification Search
CPC .... B62B 3/02; B62B 3/04; B62B 3/10; B62B 3/002; B62B 3/00; B62B 3/005; B62B 3/18; B62B 2202/56; B62B 2202/67; B62B 2202/61; A61B 19/0248; A61B 2019/025; A61B 2019/0249; A61B 2019/0256; A61B 50/10; A61B 50/13; A47B 2031/006; A47B 2031/003; A47B 57/408; A47B 57/40; A47B 57/00; A47B 57/406; A47B 57/402
See application file for complete search history.

(56) References Cited

U.S. PATENT DOCUMENTS 2,652,308 A * 9/1953 Peterson ................. B62B 3/003
                                                    280/79.11
3,654,879 A * 4/1972 Ferdinand ............ A47B 57/402
                                                    108/110
(Continued)

FOREIGN PATENT DOCUMENTS

| DE | 2856830 A1 | 7/1980 |
|---|---|---|
| DE | 102007053327 A1 | 5/2009 |

(Continued)

Primary Examiner — James M Dolak
(74) Attorney, Agent, or Firm — Whitmyer IP Group LLC

(57) ABSTRACT

A support device for releasable connection to an equipment carrier, and for supporting a medical appliance, a medical instrument or another payload, includes an engagement hook for engaging in an opening on an equipment carrier and a bolt for locking a connection between the engagement hook and an opening in which the engagement hook engages.

20 Claims, 6 Drawing Sheets

(51) Int. Cl.
*A47B 31/00* (2006.01)
*F16M 13/02* (2006.01)

(56) References Cited

U.S. PATENT DOCUMENTS

| | | | | |
|---|---|---|---|---|
| 4,064,996 A | * | 12/1977 | Shillum | A47B 57/402 108/107 |
| 4,101,108 A | * | 7/1978 | Klein | A47B 57/40 248/223.31 |
| 4,406,374 A | | 9/1983 | Yedor | |
| 4,421,239 A | * | 12/1983 | Vargo | A47B 57/404 108/107 |
| 5,022,621 A | | 6/1991 | Quest | |
| 5,065,873 A | * | 11/1991 | Tseng | A47B 57/54 108/107 |
| 5,314,243 A | | 5/1994 | McDonald et al. | |
| 5,333,746 A | * | 8/1994 | Bustos | A47B 57/00 108/109 |
| 5,450,971 A | * | 9/1995 | Boron | A47F 1/12 108/107 |
| 5,452,812 A | * | 9/1995 | Niequist | A47B 47/021 108/107 |
| 5,490,600 A | * | 2/1996 | Bustos | A47B 57/00 211/184 |
| 5,605,344 A | * | 2/1997 | Insalaco | A47B 47/02 280/47.34 |
| 5,645,182 A | * | 7/1997 | Miller, Jr. | A47F 1/12 108/107 |
| 5,695,078 A | * | 12/1997 | Otema | A47B 57/045 108/108 |
| 5,797,503 A | * | 8/1998 | Stevens | A47B 31/00 108/107 |
| 6,123,209 A | * | 9/2000 | Tseng | A47B 87/005 211/182 |
| 6,196,141 B1 | * | 3/2001 | Herron, III | A47B 57/42 108/108 |
| 6,681,705 B2 | * | 1/2004 | Wetterberg | A47B 57/40 108/107 |
| 6,773,080 B2 | * | 8/2004 | Chen | A47B 57/40 211/26 |
| 6,920,831 B2 | * | 7/2005 | Lin | A47B 57/408 108/107 |
| 6,966,267 B2 | * | 11/2005 | Bienick | A47B 57/42 108/108 |
| 7,386,954 B2 | * | 6/2008 | Korte | A01G 9/143 47/39 |
| 7,815,202 B2 | * | 10/2010 | Richards | A47F 5/135 211/126.8 |
| 7,900,781 B2 | * | 3/2011 | Baine | A47F 5/0838 211/106.01 |
| 8,042,892 B2 | * | 10/2011 | Benz | A47B 57/562 108/108 |
| 8,123,315 B2 | * | 2/2012 | Hagele | A47B 57/425 108/108 |
| 8,191,845 B1 | * | 6/2012 | Yu | A47F 5/0853 248/220.42 |
| 8,262,177 B2 | * | 9/2012 | Picken | F25D 25/024 312/408 |
| 8,622,494 B2 | * | 1/2014 | Picken | F25D 25/024 312/408 |
| 8,881,660 B2 | * | 11/2014 | Simpson | A47F 5/00 108/108 |
| 8,964,359 B2 | * | 2/2015 | Bauer | A61G 12/004 361/624 |
| 9,084,485 B2 | * | 7/2015 | Sukman | A47B 96/06 |
| 9,237,803 B2 | * | 1/2016 | Kassanoff | A47B 47/0091 |
| 9,532,663 B2 | * | 1/2017 | Nilsson | B25H 3/04 |
| 9,539,160 B2 | * | 1/2017 | Emmerich | A61G 12/002 |
| 9,655,443 B2 | * | 5/2017 | Cano | A47B 57/404 |
| 9,655,448 B2 | * | 5/2017 | Tiilikainen | A47B 96/024 |
| 9,752,821 B2 | * | 9/2017 | Seeley | F25D 25/024 |
| 9,770,103 B2 | * | 9/2017 | Cochran | A47B 46/005 |
| 9,781,998 B2 | * | 10/2017 | Mogensen | A47B 57/402 |
| 9,808,316 B2 | * | 11/2017 | Hasegawa | A61B 50/10 |
| 9,814,310 B2 | * | 11/2017 | Kassanoff | A47B 47/0091 |
| 2004/0108427 A1 | | 6/2004 | Chen et al. | |
| 2007/0042638 A1 | * | 2/2007 | Choi | A47B 57/402 439/541.5 |
| 2007/0158517 A1 | * | 7/2007 | King | A47F 5/0006 248/301 |
| 2008/0030114 A1 | * | 2/2008 | Becke | A47B 57/425 312/408 |
| 2013/0146551 A1 | | 6/2013 | Simpson et al. | |

FOREIGN PATENT DOCUMENTS

| | | |
|---|---|---|
| DE | 202010007467 U1 | 10/2010 |
| EP | 1238884 A1 | 9/2002 |
| EP | 2110209 A2 | 10/2009 |
| GB | 2044079 A | 10/1980 |
| WO | 2007077609 A1 | 7/2007 |

* cited by examiner

Fig. 5
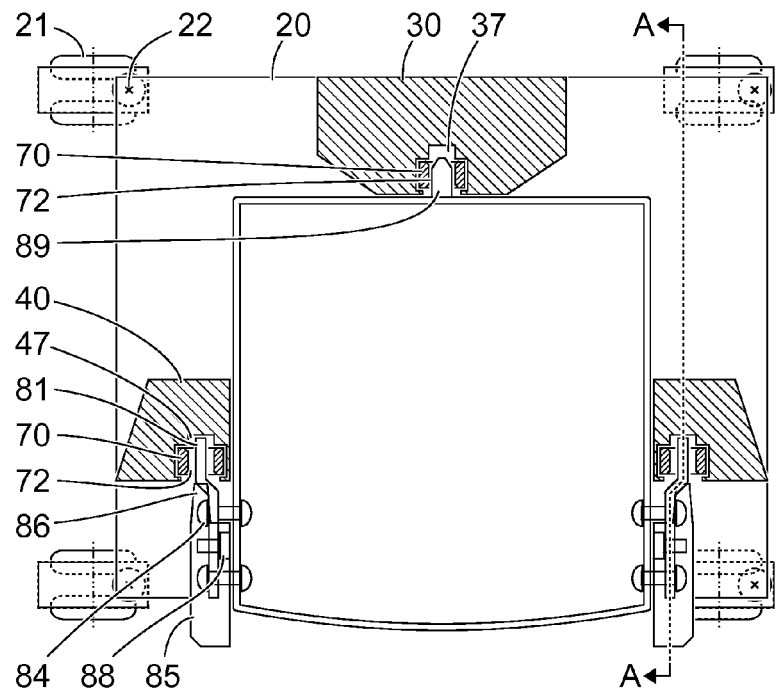
Fig. 6  A-A
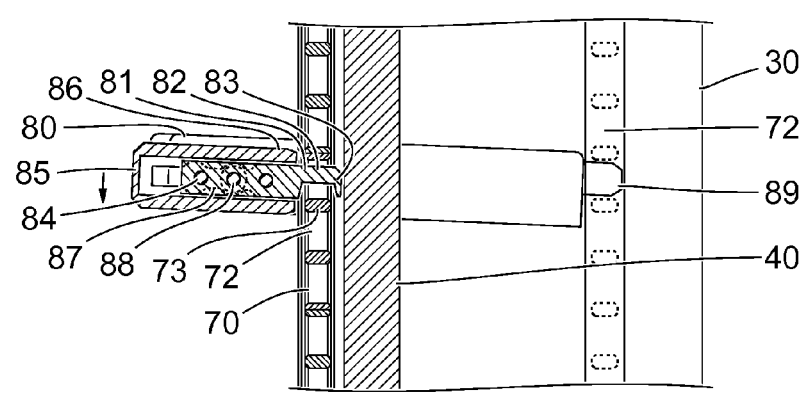

EQUIPMENT TROLLEY

FIELD OF THE INVENTION

The present invention relates to an equipment trolley or another equipment carrier and to a support device for mounting on an equipment carrier and for supporting a medical appliance, a medical instrument or another payload in a medical treatment room.

BACKGROUND OF THE INVENTION

In operating theaters and other medical treatment rooms, many medical appliances and instruments are often used simultaneously or one after another. A medical equipment carrier, in particular a medical equipment trolley, i.e. a medical equipment carrier that can be moved on wheels, may allow a large number of medical appliances and instruments to be arranged in an economically and ergonomically favorable and flexible way.

A medical equipment trolley or another medical equipment carrier is intended not only to be robust and to allow easy cleaning and sterilization, but also to be able to be modified or changed (in particular extended) with little effort and to be able to be assembled safely and correctly, as far as possible even by persons without technical training. A medical equipment carrier should be able to be adapted to new tasks, in particular with little effort, by replacing support devices or storage elements or by moving them about. In particular, on the one hand, support devices or storage elements should be able to be assembled and disassembled without tools and, on the other hand, in the assembled state, should be firmly connected in a reliable manner to the medical equipment carrier.

SUMMARY OF THE INVENTION it is an object of the present invention to make available an improved support device, for mounting on an equipment carrier and for supporting a medical appliance, a medical instrument or another payload, and an improved medical equipment carrier.

This object is achieved by the subjects of the independent claims.

Developments are set forth in the dependent claims.

A support device for releasable connection to an equipment carrier, and for supporting a medical appliance, a medical instrument or another payload, comprises an engagement hook for engaging in an opening on an equipment carrier and a bolt for locking a connection between the engagement hook and an opening in which the engagement hook engages.

The support device is intended in particular to be mounted on a mobile equipment carrier, or an equipment trolley, for medical or non-medical uses or on a stationary equipment carrier for medical or non-medical uses. The engagement hook is intended in particular to engage in one of several openings on an equipment carrier, in order to releasably connect the support device to the equipment carrier in one of several alternative positions. The support device can have one or more further engagement hooks and, on each engagement hook, a bolt can be provided for locking a connection between the further engagement hook and an opening. Moreover, the support device can have one or more pins, lugs or other mechanisms for stabilizing the support device on further openings or steps on the equipment carrier.

By inserting the engagement hook into an opening on an equipment carrier, the support device can be suspended quickly on an equipment carrier in one position or in one of several alternative positions. The bolt permits a locking of the connection between the engagement hook and an opening in which the engagement hook engages, and it permits subsequent unlocking of the connection without a tool, The support device can therefore be moved about or exchanged quickly and with lithe effort, in order to modify an equipment carrier or adapt it to new tasks.

In a support device as described here, the engagement hook has in particular a straight portion for engaging in an opening, and a portion which is angled in relation to the straight portion and is for engaging behind an edge of the opening, wherein the bolt is movable, parallel to the straight portion of the engagement hook, between an unlocking position and a locking position.

The engagement hook thus has in particular an L-shaped configuration. In the intended use of the support device, in particular, the straight portion is arranged horizontally or substantially horizontally, and the portion angled in relation to the straight portion is arranged vertically or substantially vertically. The portion angled in relation to the straight portion is provided and designed in particular for engagement behind a web between two openings in a row of openings. In the locking position, the bolt is in particular arranged such that it suppresses a movement of the engagement hook in a direction orthogonal to the straight portion or parallel or substantially parallel to the angled portion. In this way, in its locking position, the bolt is able to ensure that the portion of the engagement hook angled in relation to the straight portion cannot be moved out of its position engaging behind the edge of the opening.

The engagement hook and the bolt are designed in particular in such a way that the engagement hook in the opening on an equipment carrier can be moved in a direction orthogonal to a straight portion of the engagement hook only when the bolt is in its unlocking position. In the locking position, the bolt holds the engagement hook in particular in a position, relative to the opening, in which a portion of the engagement hook angled in relation to the straight portion engages behind an edge of the opening.

In a support device as described here, the bolt is in particular provided and designed such that, in the unlocking position, it is not arranged or not substantially arranged next to the straight portion of the engagement hook and, in the locking position, it is arranged next to the straight portion of the engagement hook.

In its locking position, the bolt is in particular arranged at least partially inside the same opening in which the engagement hook, in particular optionally the straight portion thereof, is arranged. Alternatively, the bolt can be provided and arranged such that, in its locking position, it engages in another opening, in particular in an adjacent opening.

In a support device as described here, the bolt is in particular provided and designed such that, in the unlocking position, it does not engage or does not substantially engage in an opening on an equipment carrier in which the engagement hook engages, and, in the locking position, it does engage in an opening on an equipment carrier in which the engagement hook engages.

A support device as described here in particular also comprises a safety mechanism for holding the bolt in the locking position.

In a support device as described here, the safety mechanism is in particular designed to hold the bolt locked in the locking position.

In addition, the safety mechanism can be designed also to hold the bolt in its unlocking position by means of elastic latching or in some other way. The safety mechanism is in particular provided and designed such that, when moving the bolt between its locking position and its unlocking position (and optionally also in the opposite direction), a mechanical resistance has to be overcome.

The safety mechanism comprises, for example, one or more cams on the bolt, which cams can engage in one or more grooves on the support device when the bolt is located in the locking position. Alternatively, one or more cams can be provided on the support device and one or more grooves on the bolt, or cams can be provided both on the support device and also on the bolt. An elasticity of the cam or cams or of the groove or grooves allows the cams and groove to slide past each other when the elastic counterforce is overcome.

In a support device as described here, the safety mechanism is in particular designed to generate an at least either tactile or acoustically perceptible signal when the bolt is moved to the locking position.

The safety mechanism generates in particular a tactile signal that is perceptible to a person manually moving the bolt. Alternatively or in addition, the safety mechanism generates a click or another acoustically perceptible signal when the bolt adopts the locking position.

A support device as described here in particular also comprises a spar for supporting a medical appliance or a medical instrument or another payload, wherein the spar is connectable to the engagement hook, wherein the bolt is rigidly connected to the spar, wherein the bolt, in the locking position, engages through a bore on the engagement hook, wherein, in the locking position of the bolt, the spar is pivotable between a loose position and a stable position about an axis extending through the bolt, wherein, in the loose position of the spar, the bolt is movable between its locking position and its unlocking position and the spar can be separated from the engagement hook, and wherein, in the stable position of the spar, the spar is mechanically connected to the engagement hook and is loaded with a payload.

The support device comprises two parts or units which are separate, but which are connected to each other in the stable position of the spar. The first unit comprises the spar and the bolt, which extend in two directions that are in particular parallel or substantially parallel to each other. The second unit comprises the engagement hook and the bore. When the boll is inserted into the bore or engages through the bore, the first unit is pivotable relative to the second unit about an axis which is defined by the bolt and the bore and which in particular is parallel to the bolt and to the spar. To connect the support device to an equipment carrier, the engagement hook is first of all inserted into or suspended in an opening on the equipment carrier. Thereafter, the bolt is brought with a linear movement through the bore on the engagement hook into its locking position, which in particular lies in the same opening or in an adjacent opening, At the end of this linear movement, the first unit is located relative to the second unit in the loose position in which it can be separated again from the second unit by a linear movement in the opposite direction. From the loose position, the first unit can be pivoted to the stable position in which the first part and the second part are connected to each other and in particular can no longer be pulled apart.

A support device as described here in particular also comprises a first plate, which is rigidly connected to the engagement hook and has the bore, and a second plate, which is rigidly connected to the spar and to the bolt, wherein the first plate and the second plate are connected to each other with a form fit in the stable position.

The form fit connection of the two plates is effected, for example, by screws or other mushroom-shaped means on one of the two plates which engage in slits on the other plate.

A support device as described here in particular also comprises a cover cap or a bracket that can be turned over the first plate and the second plate in order to hold the second plate relative to the first plate in the stable position.

The first plate and the second plate have in particular a similar or substantially identical configuration. For example, the first plate and the second plate are each rectangular with the same linear dimensions. The support device is in particular designed such that the first plate and the second plate lie one over the other substantially congruently in the stable position of the spar. The cover chamber or the bracket bears on opposite edges or on all edges of the first plate and of the second plate and thus holds the second plate relative to the first plate with a form fit and thus also holds the spar in the stable position.

An equipment carrier for carrying a medical appliance, a medical instrument or another payload comprises a supporting framework and an opening on the supporting framework, wherein the opening is provided and designed for receiving an engagement hook on a support device.

The equipment carrier is in particular an equipment trolley for medical or non-medical uses with one or more rollers or wheels for conveying the weight of the equipment carrier into a floor on which the equipment carrier stands, wherein the wheels or rollers permit low-friction movement of the equipment carrier on the floor. Alternatively, the equipment carrier is provided for a stationary medical or non-medical use. The equipment carrier is in particular provided and designed to carry a medical appliance, a medical instrument or another payload indirectly by means of a support device connected to the equipment carrier via the opening. The supporting framework comprises in particular one or more vertical or substantially vertical columns or spars, which can be connected by a base, a bridge and/or other horizontal devices.

In an equipment carrier as described here, a plurality of openings in particular are provided on the supporting framework, wherein an engagement hook on a support device can engage alternately in one of the plurality of openings.

The openings are in particular arranged in a row one above the other and with uniform intervals between them, e.g. in a grid.

An equipment carrier as described here in particular comprises several columns, each one with an opening for receiving an engagement hook on a support device.

In an equipment carrier as described here, the supporting framework in particular comprises several columns, with several respective openings provided on each of the columns, wherein respective openings with different markings are provided on each column, and wherein openings which receive hook devices of the support device simultaneously, in an intended arrangement of a support device, have identical or corresponding markings.

An intended arrangement of a support device is in particular a horizontal arrangement or an arrangement of the support device parallel to a floor surface on which the equipment carrier stands. The different markings are in particular differently colored markings. For example, each column has several holding devices, each of these with one or more openings, wherein adjacent holding devices have different colors.

An equipment carrier as described here in particular also comprises a support device as described here.

An equipment carrier as described here comprises in particular several columns, each with an opening, wherein several engagement hooks are provided on the support device and are designed to engage simultaneously in a respective opening.

In an equipment carrier as described here, the openings on the columns and the engagement hooks and the bolts on the support device are in particular designed such that at least either an insertion of the engagement hooks on the support device into a respective opening on the columns or a locking of the connection between an engagement hook and an opening is possible only when the support device adopts one of several intended positions.

Intended positions of the support device are in particular positions in which the support device is arranged horizontally or parallel with respect to a floor surface on which the equipment carrier stands. The equipment carrier and the support device are thus designed such that an oblique or incorrect connection of the support device to the equipment carrier is not possible.

BRIEF DESCRIPTION OF THE DRAWINGS

Embodiments are explained in more detail below with reference to the attached figures, in which:

FIG. 5 shows a further schematic view of the medical equipment trolley from FIGS. 1 to 4;

FIG. 6 shows a further schematic view of a vertical section through the medical equipment trolley from FIGS. 1 to 5;

DETAILED DESCRIPTION OF THE INVENTION

Figure 1:
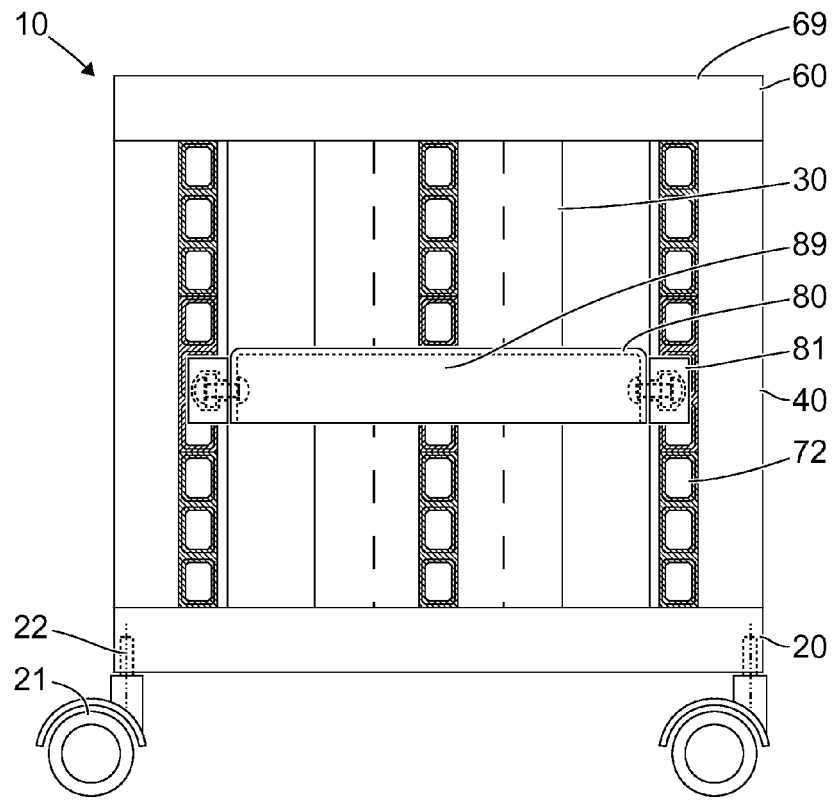
FIG. 1 shows a schematic view of a medical equipment trolley.

FIG. 1 shows a schematic view of a medical equipment carrier, in particular a medical equipment trolley 10. The drawing plane of FIG. 1 is vertical or, in the intended use of the medical equipment trolley 10, orthogonal to a horizontal floor surface on which the medical equipment trolley 10 stands.

The medical equipment trolley 10 comprises several surface modules, namely a base 20, a bridge 60 and a shelf 80 as support device for medical appliances and instruments, and also several columns 30, 40. The surface modules 20, 60, 80 extend substantially parallel to the floor surface on which the medical equipment trolley 10 stands and therefore orthogonal to the drawing plane of FIG. 1. The columns 30, 40 extend substantially orthogonally with respect to the surface modules 20, 60, 80 and parallel to the drawing plane of FIG. 1.

In the intended use of the medical equipment trolley 10, the base 20 is arranged at the bottom. A roller unit 21 is arranged on the underside of the substantially rectangular base 20, at each corner of the base 20. Each roller unit 21 comprises in particular two rollers and is pivotable about a vertical pivot axis 22, such that the medical equipment trolley can be pushed and rotated in any desired directions with low friction. In the example shown, the bridge 60 forms the upper end of the medical equipment trolley 10.

The medical equipment trolley 10 has a front face, which is intended to be directed toward medical personnel and which, in the view n FIG. 1, is directed toward the observer. The rear face of the medical equipment trolley lies opposite the front face and, in the view in FIG. 1, is directed away from the observer. From the direction of the front face, the shelf 80 can be inserted into the medical equipment trolley 10, and, from the direction of the front face, access can be made to medical appliances or instruments placed or mounted or stored on or in the medical equipment carrier 10.

A first column 30 is arranged centrally on the rear face of the medical equipment trolley 10. The second columns 40 are arranged symmetrically with respect to each other on the sides of the medical equipment trolley 10, near the front face of the medical equipment trolley 10. Each column 30, 40 has a plurality of openings 72, The openings 72 are arranged on each column 30, 40 in a regular grid pattern and are each open in the direction of the front face of the medical equipment trolley 10.

The shelf 80 has one or more pins 89 and two or more engagement hooks 81, which are designed facing the openings 72 and are intended to engage in a respective opening 72. Accordingly, the one or more pins 89 and the engagement hooks 81 in the view in FIG. 1 are directed away from the observer and are concealed by other parts of the shelf 80, for which reason they are only indicated in FIG. 1 by a broken-line contour. The one or more pins 89 are arranged centrally or near the center on the rear edge of the shelf 80 so as to engage in a respective opening 72 in the first column 30. In a departure from the view in FIG. 1, the first column 30 can have two or more vertical rows of openings 72. The engagement hooks 81 are provided, arranged and designed to engage in a respective opening 72 in the laterally arranged second columns 40.

The shelf 80 can be arranged at different heights or at different distances from the base 20 and from the bridge 60. On one or on both of the engagement hooks 81 and/or on the pin 89, devices (not shown in FIG. 1) are provided for locking the shelf 80 on the columns 30, 40, which are not shown in FIG. 1. In particular, one or both engagement hooks 81 and/or the pin 89 are each locked in an opening 72, such that the shelf 80 is prevented from accidentally coming loose from its intended position and then falling.

The medical equipment trolley 10 can be modified by replacing or supplementing the shelf 80 with one or more modules with drawers, and/or open compartments or compartments closable with flaps or doors, and/or further shelves 80. In the configuration shown, medical appliances, medical instruments and/or other payload can be arranged in particular on the base 20 and on the shelf 80 and optionally also on the bridge 60.

Figure 2:
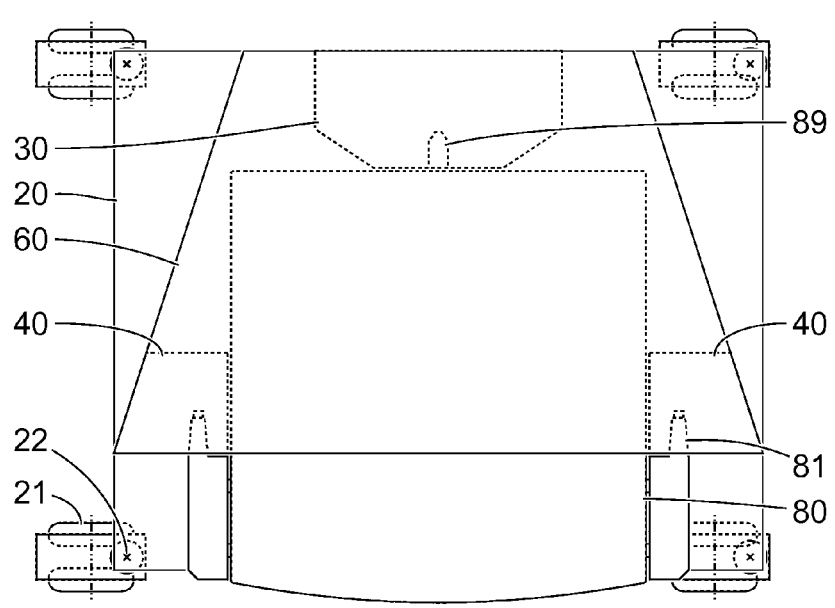
FIG. 2 shows a further schematic view of the medical equipment trolley from FIG. 1.

FIG. 2 shows a further schematic view of the medical equipment trolley 10 from FIG. 1. FIG. 2 shows a plan view, i.e. the drawing plane of FIG. 2 is horizontal or parallel to a floor surface on which the medical equipment trolley 10 stands in its intended arrangement, and therefore orthogonal to the drawing plane of FIG. 1. The rear face of the medical equipment trolley 10 facing away from the observer in the view in FIG. 1 lies at the top in FIG. 2, and the front face of the medical equipment trolley 10 facing toward the observer in the view in FIG. 1 lies at the bottom in the view in FIG. 2.

The rectangular basic shape of the base 20 with a respective roller unit 21 at each corner can be seen in FIG. 2. The vertical pivot axes 22 of the roller units 21 are orthogonal to the drawing plane of FIG. 2.

Above the base 20, the columns 30, 40 extend substantially orthogonally with respect to the drawing plane of FIG. 2. Each column 30, 40 has a substantially polygonal cross section. The first column 30 is arranged centrally on the rear face of the medical equipment trolley. The second columns 40 are designed symmetrically to each other and are arranged symmetrically to each other on the sides of the medical equipment trolley 10. In the example shown, the second columns 40 are arranged closer to the front face than to the rear face of the medical equipment trolley 10. In the viewing direction of FIG. 2, the columns 30, 40 are concealed by the bridge 60. For this reason, only the outer contours of the cross sections of the columns 30, 40 are indicated by broken lines in FIG. 2.

In the example shown, the bridge 60 has a substantially trapezoidal basic shape and, in the viewing direction of FIG. 2, conceals part of the shelf 80, which is therefore indicated only by broken lines.

The shelf 80 has engagement hooks 81 which are arranged symmetrically to each other on both sides and which engage in corresponding openings 72 (cf. FIG. 1) in the second columns 40. Moreover, the shelf 80 has a pin 89, which engages in a corresponding opening 72 (cf. FIG. 1) in the first column 30.

Figure 3:
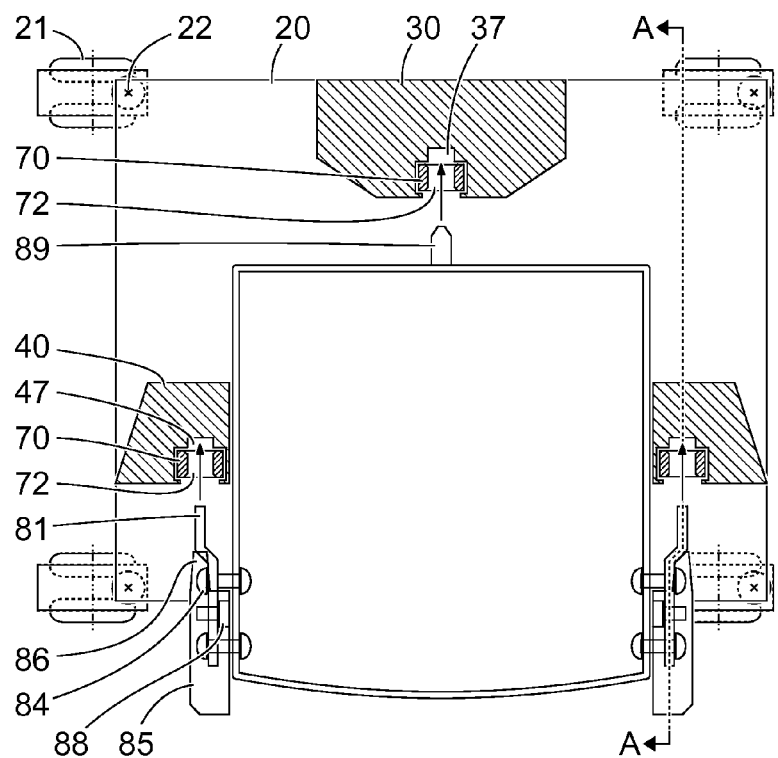
FIG. 3 shows a further schematic view of the medical equipment trolley from FIGS. 1 and 2.

FIG. 3 shows a further schematic view of the medical equipment trolley 10 from FIGS. 1 and 2. The orientation of the drawing plane of FIG. 3 corresponds to that of FIG. 2. In contrast to FIG. 2, the bridge 60 is not shown in FIG. 3, and the columns 30, 40 are shown in section along a horizontal plane. Moreover, parts of the shelf 80 are depicted as transparent in order to reveal their inner structure.

Toward the front face of the medical equipment trolley 10, the columns 30, 40 each have open channels 37, 47, in which grid bars 70 are arranged. The channels 37, 47 are designed such that the grid bars 70 are held with a form fit in the channels 37, 47. Alternatively or in addition, the grid bars 70 can be held by screws, rivets or otherwise in the channels 37, 47 of the columns 30, 40 with a form fit, a cohesive fit or a frictional fit. Moreover, in a departure from the view in FIG. 3, the openings 72 may be formed directly in the columns 30, 40, for example in the form of rows of bores.

Several grid bars 70 are inserted in each channel 37, 47 on a column 30, 40, wherein each grid bar 70 has one or more openings 72. The grid bars 70 in the channel 37, 47 of a column 30, 40 have different markings, in particular different colors. This is indicated in FIG. 1 by different hatchings (i.e. in one case from top left to bottom right, and in the other case from bottom left to top right). The markings are chosen such that corresponding openings 72 on different columns 30, 40 are identically marked, i.e. openings 72 in which the engagement hooks 81 and pin 89 simultaneously engage in the intended and in particular horizontal arrangement of the shelf 80. Upon insertion of the shelf 80, the markings facilitate the correct insertion of the engagement hooks 81 and of the pin 89 into the openings 72 and reduce the risk of incorrect positioning, in particular oblique positioning, of the shelf 80.

The cross sections of the columns 30, 40 are shown uniformly and very much simplified in FIG. 3. In a departure from the view in FIG. 3, the columns 30, 40 are formed from or composed of profile parts made of metal and/or plastic, in particular extruded profiles. In the inside of the columns 30, 40, hollow spaces or channels can be provided for the arrangement of fluid conduits and lines for electrical or optical transmission of power and/or data.

In FIG. 3, the shelf 80 is shown in a position in which it is not yet connected to the columns 30, 40 of the medical equipment trolley 10. In particular, the engagement hooks 81 on the sides of the shelf 80 and the pin 89 on the rear edge of the shelf 80 do not yet engage in the openings 72. Arrows indicate a movement of the shelf 80, in particular of the engagement hooks 81 and of the pin 89, into the openings 72, with which movement the shelf 80 can be connected mechanically to the columns 30, 40 and thus to the medical equipment trolley 10.

The engagement hooks 81 are formed, for example, by sheet metal strips, in the example shown by bent metal strips. Each engagement hook 81 is rigidly connected to the shelf 80 by means of two rivets 84. One or more screw heads 88 of screws are arranged between the rivets and between the engagement hook 81 and the shelf 80 in each case, which screws are screwed either into the engagement hook 81 or into the edge of the shelf 80. The function of this screw head 88 is described with reference to FIGS. 4, 6 and 8 and, in particular, FIG. 9.

A slide 85 with two bolts 86 is arranged on each engagement hook 81. The slide 85 is depicted as transparent or is indicated only by its outer contours so that features concealed by it are made visible. Each slide 85 is movable between an unlocking position shown in FIG. 3 and a locking position. The action of the bolt 86 on the slide 85 is described in particular with reference to FIG. 9.

Figure 4:
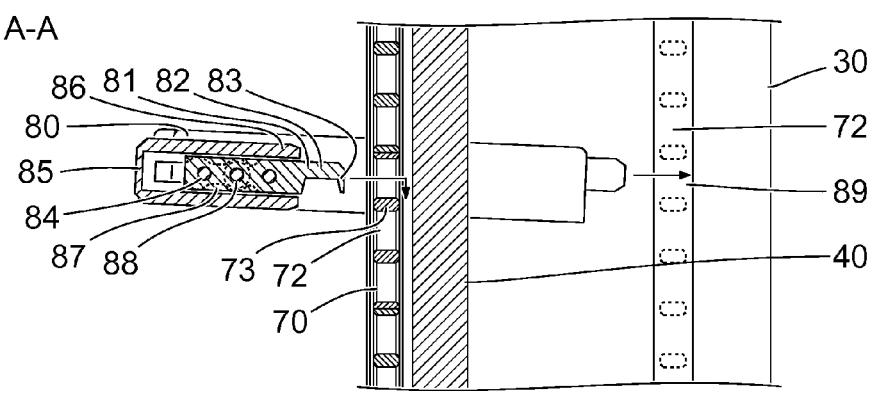
FIG. 4 shows a schematic view of a vertical section through the medical equipment trolley from FIGS. 1 to 3.

FIG. 4 shows a schematic view of a cross section along the surface A-A indicated in FIG. 3. The surface A-A is vertical and therefore orthogonal to the drawing plane of FIG. 3.

The engagement hook 81 has a straight portion 82, and a portion 83 that is angled in relation to the straight portion 82. The screw with the screw head 88 is arranged between the rivets 84. The contour of the screw head 88 and edges of the slide 85, which are concealed by the structural part forming the engagement hook 81, are indicated by broken lines. Insofar as it does not form the bolts 86, the slide 85 has a C-shaped cross section, which engages behind the structural part forming the engagement hook 81.

The edges of the slide 85 that are indicated by broken lines form several locking lugs 87, which interact with the screw head 88. By virtue of the interaction between the locking lugs 87 on the slide 85 and the screw head 88, the slide 85 and in particular the bolts 86 are held in the unlocking position shown in FIGS. 3 and 4 and in the locking position described with reference to FIG. 9.

An angled arrow indicates how the engagement hook 81 can be inserted into an opening 72 in a grid bar 70 in the column 40. A further arrow indicates how at the same time the pin 89 on the rear edge (in FIG. 4 the right-hand edge) of the shelf 80 can be inserted into an opening 72 in the column 30.

FIG. 5 shows a further schematic view of the medical equipment trolley 10 from FIGS. 1 to 4. The nature of the view and in particular the orientation of the drawing plane correspond to those of FIG. 3.

FIG. 5 shows the shelf 80 in a position in which the engagement hooks 81 and the pin 89 are already inserted in three corresponding openings in grid bars 70 in the columns 30, 40.

FIG. 6 shows a further schematic view of the medical equipment trolley from FIGS. 1 to 5. The nature of the view corresponds to that of FIG. 4. The situation shown corresponds to that of FIG. 5. The engagement hook 81 engages fully in an opening 72 in a grid bar 70 in a second column 40, wherein it engages completely through the grid bar 70. The pin 89 likewise engages in a corresponding opening 72 in the first column 30.

Figure 7:
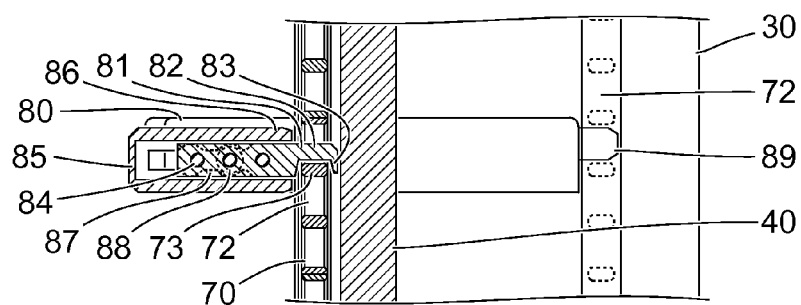
FIG. 7 shows a further schematic view of a vertical section through the medical equipment trolley from FIGS. 1 to 6.

FIG. 7 shows a further schematic view of the medical equipment trolley from FIGS. 1 to 6. The nature of the view corresponds to that of FIGS. 4 and 6. Compared to the situation shown in FIG. 6, the shelf 80 is lowered according to the arrow in FIG. 6, such that the straight portion 82 of the engagement hook 81 bears on a web 73 between two openings 72 in the grid bar 70 in the second column 40, and the portion 83 of the engagement hook 81 at an angle relative to the straight portion 82 engages behind the web 73. In this way, a separation of the shelf 80 from the columns 30, 40 by a purely horizontal movement is suppressed by a form fit.

Figure 8:
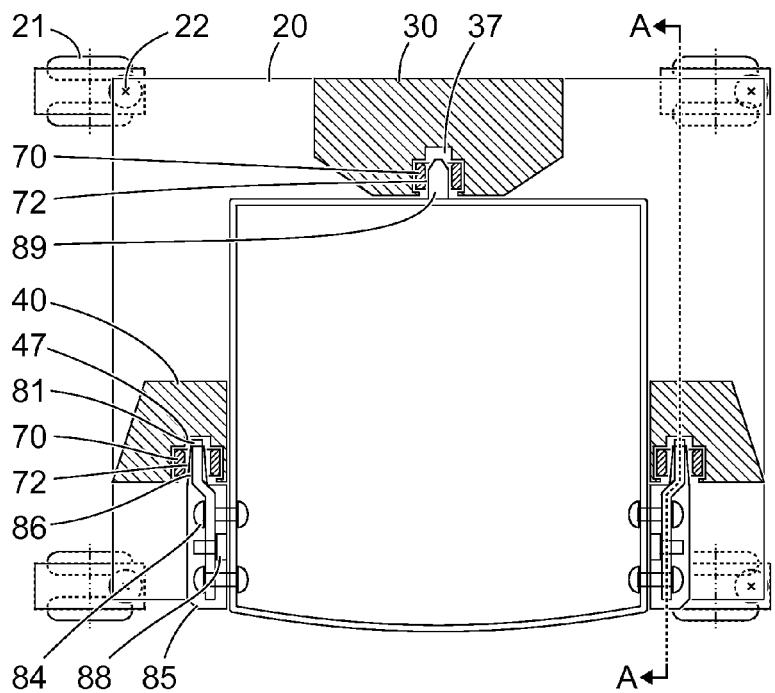
FIG. 8 shows a further schematic view of the medical equipment trolley from FIGS. 1 to 7.

FIG. 8 shows a further schematic view of the medical equipment trolley from FIGS. 1 to 7. The nature of the view corresponds to that of FIGS. 3 and 5. The situation shown in FIG. 8 differs from that shown in FIG. 7 in that the slides 85 with the bolts 86 are pushed into a locking position in which the bolts 86 engage in openings 72 in the columns 40.

Figure 9:
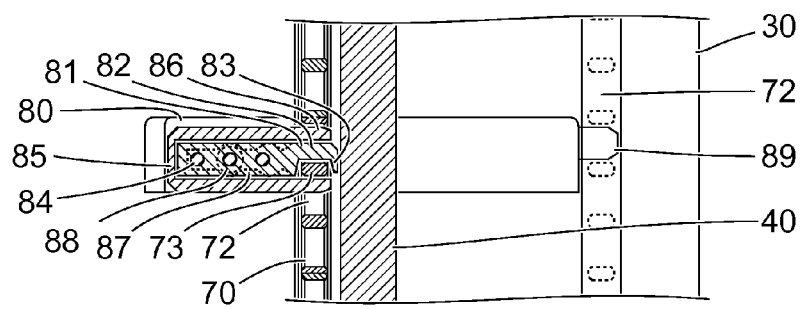
FIG. 9 shows a further schematic view of a vertical section through the medical equipment trolley from FIGS. 1 to 8.

FIG. 9 shows a further schematic view of the medical equipment trolley from FIGS. 1 to 8. The nature of the view corresponds to that of FIGS. 4, 6 and 7. The situation shown corresponds to the situation shown in FIG. 8. One of the two bolts 86 on the slide 85 engages in the same opening 72 in which the engagement hook 81 engages. The second bolt 86 engages in an adjacent opening 72. Each individual bolt 86 already in itself suppresses a movement of the slide 85 and therefore also a movement of the engagement hook 81 in the vertical direction. In this way, the bolts 86 lock the engagement hook 81 in the position shown in FIG. 9, in which the portion 83 of the engagement hook 81 at an angle relative to the straight portion 82 engages behind the web 73. The shelf 80 can no longer be detached from the columns 30, 40. The shelf 80 can be detached again from the columns 30, 40 only when the slide 85 with the bolts 86 is pushed back to the unlocking position shown in FIGS. 3 to 7.

Figure 10:
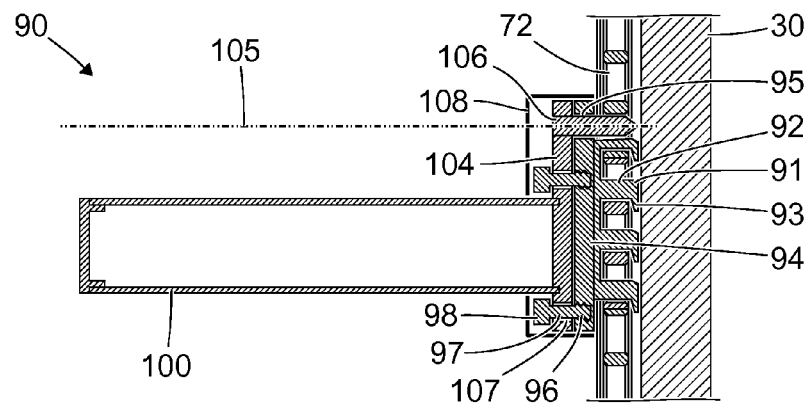
FIG. 10 shows a schematic view of an equipment rail.

FIG. 10 shows a schematic view of a further support device, namely an equipment rail 90 on a column 30 of the medical equipment trolley from FIGS. 1 to 9. The equipment rail 90 can be connected to the medical equipment trolley 10 as an alternative or in addition to the shelf described with reference to FIGS. 3 to 9. The equipment rail 90 comprises a spar 100 which, in the intended use of the equipment rail 90, is arranged in particular horizontally or substantially horizontally and therefore orthogonally with respect to the column 30. The equipment rail 90 comprises several engagement hooks 91, each with a straight portion 92 and with a portion 93 angled in relation to the straight portion 92. The engagement hooks 91 are similar to or correspond in particular to the engagement hooks of the shelf described with reference to FIGS. 3 to 9. The engagement hooks 91 are rigidly connected to a first plate 94, for example joined by welding or soldering. A bore 95 is provided in the first plate 94. Two screws 96 are provided on the side of the first plate 94 facing away from the engagement hooks 91. The screws 96 are inserted into the first plate 94 such that not only their heads 98 but also respectively part of their shank 97 protrudes from the first plate 94.

The equipment rail 90 further comprises a second plate 104, to which the spar 100 is rigidly connected. The screws 96 connected to the first plate 94 engage through slits 107 in the second plate 104, wherein the shanks 97 of the screws 96 lie in the slits 107, and the heads 98 of the screws 96 on the one hand and the first plate 94 on the other hand bear on opposite sides of the second plate 104. A pin 106 is rigidly connected to the second plate 104, in particular being inserted into a corresponding bore in the second plate 104 and being connected thereto with a frictional fit, cohesive fit and/or form fit. The pin 106 protrudes from the second plate 104 in a direction counter to the spar 100. The pin 106 is rotationally symmetrical with respect to a horizontal axis 105.

The pin 106 engages through the bore 95 in the first plate 94 and into an opening 72 on the column 30, into which one of the engagement hooks 91 engages in particular at the same time. The pin 106 acts as a bolt which, in its locking position shown in FIG. 10, provides a form fit that suppresses a lifting of the engagement hook 91 and therefore a separation of the equipment rail 90 from the column 30. A cover cap 108 encloses the plates 94, 104 and secures their connection described below.

The way in which the equipment rail 90 can be connected to the column 30 is described below with reference to FIGS. 11 to 16.

Figure 11:
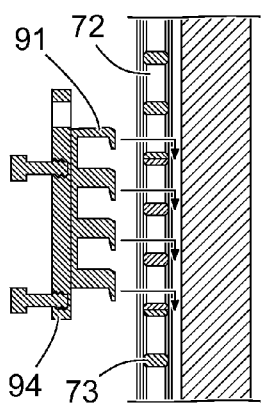
FIG. 11 shows a schematic view of part of the equipment rail from FIG. 10.

FIG. 11 shows a schematic cross-sectional view of the column 30 and of the first plate 94 with the engagement hooks 91 and the screws 96. The nature of the view, in particular the sectional plane, corresponds to that of FIG. 10.

FIG. 11 shows a situation in which the first plate 94 and the engagement hooks 91 are spaced apart from the column 30. Arrows indicate a movement with which the engagement hooks 91 can be inserted into openings 72 in grid bars 70 in the column 30.

Figure 12:
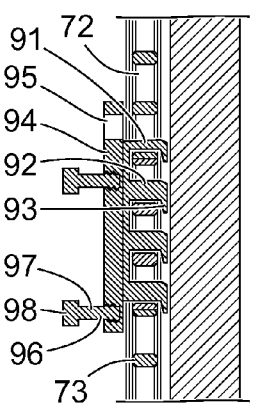
FIG. 12 shows a further schematic view of part of the equipment rail from FIGS. 10 and 11.

FIG. 12 shows a further schematic cross-sectional view of the column 30 and of the first plate 94 with the engagement hooks 91. The nature of the view, in particular the sectional plane, corresponds to that of FIGS. 10 and 11.

In FIG. 12, the hooks 91 are inserted into openings 72 in accordance with the arrows in FIG. 11. For this purpose, the engagement hooks 91 were first of all inserted completely into the openings 72 with a horizontal movement parallel to the straight portions 92 of the engagement hooks 91, after which, by means of a vertical movement, the portions 93 at an angle in relation to the straight portions 92 were moved behind the webs 73 between the openings 72, such that the angled portions 93 engage behind the webs 73.

Figure 13:
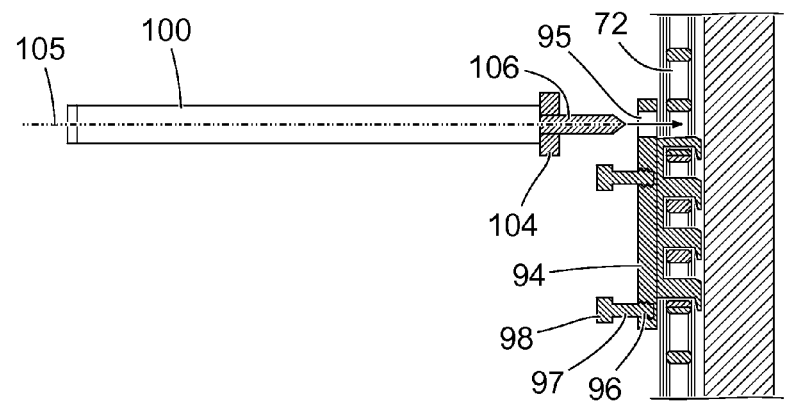
FIG. 13 shows a further schematic view of the equipment rail from FIGS. 10 to 12.

FIG. 13 shows a further schematic cross-sectional view of the equipment rail 90 from FIGS. 10 to 12. The nature of the view, in particular the sectional plane, corresponds to that of FIGS. 10 to 12.

An arrow indicates how, by means of a horizontal movement of the unit composed of spar 100, second plate 104 and pin 106, the pin 106 can be inserted through the opening 95 in the first plate 94 and into an opening 72 in the grid bar 70. The inherently rigid unit composed of spar 100, second plate 104 and pin 106 is rotated here about the axis 105 by an angle of approximately 90 degrees with respect to the position shown in FIG. 10.

Figure 14:
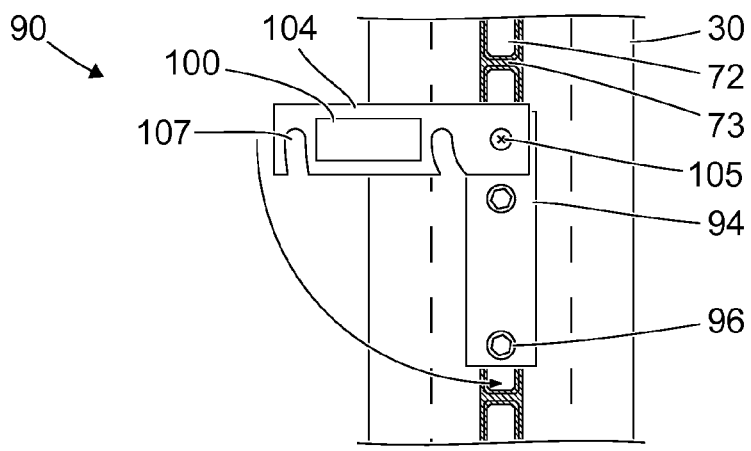
FIG. 14 shows a further schematic view of the equipment rail from FIGS. 10 to 13.

FIG. 14 shows a further schematic view of the equipment rail 90 from FIGS. 10 to 13. The nature of the view corresponds to that of FIG. 1, while the situation shown corresponds to the one shown in FIG. 13.

The second plate 104 has two slits 107 for receiving the shanks 97 (cf. FIGS. 10 to 13) of the screws 96. After the pin 106 has been inserted fully through the bore 95 in the first plate 94 and into an opening 72, i.e. when the second plate 104 bears on the first plate 94, the unit composed of spar 100, second plate 104 and pin 106 can be pivoted about the axis 105 defined by the pin 106 and the bore 95 (cf. FIGS. 10 to 13) in the first plate 94. This pivoting movement is indicated in FIG. 14 by an arrow.

Figure 15:
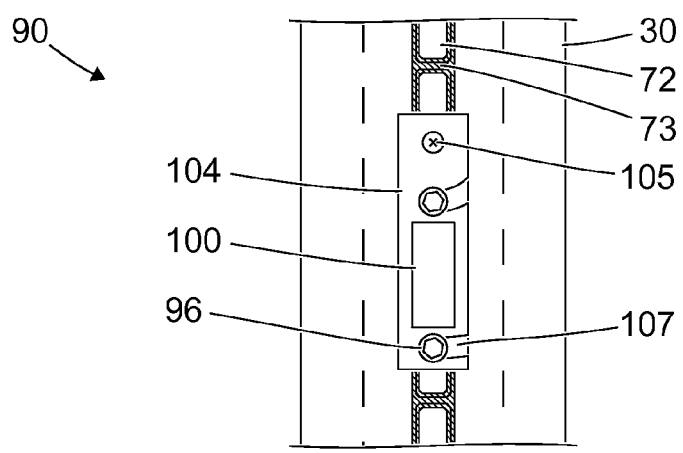
FIG. 15 shows a further schematic view of the equipment rail from FIGS. 10 to 14.

FIG. 15 shows a further schematic view of the equipment rail from FIGS. 10 to 14. The nature of the view, in particular the orientation of the drawing plane, corresponds to that of FIG. 14. FIG. 15 shows the stable position, also shown in FIG. 10, after the unit composed of spar 100, second plate 104 and pin 106 has been pivoted according to the arrow shown in FIG. 14. In this stable position, the shanks 97 (cf. FIGS. 10 to 13) of the screws 96 engage through the slits 107 in the second plate 104, and the heads 98 of the screws 96 hold the second plate 104 with a form fit on the first plate 94. The form fit between the screws 96 on the first plate 94, on the one hand, and the slits 107 of the second plate 104, on the other hand, permits not only a transfer of forces and moments from the spar 100 to the engagement hooks 91, it furthermore also holds the pin 106 in its position locking the connection between engagement hook 91 and openings 72.

Figure 16:
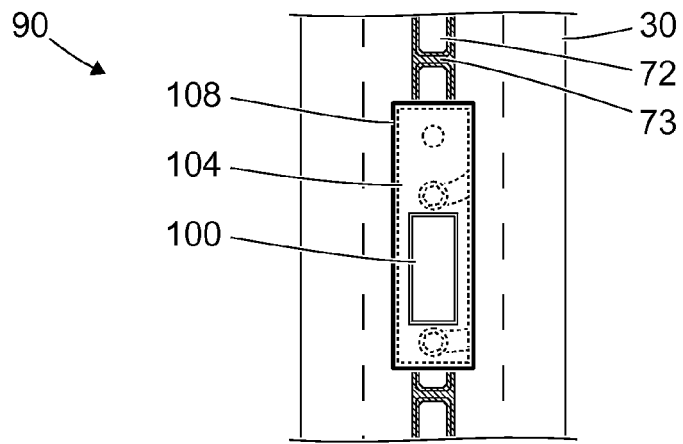
FIG. 16 shows a further schematic view of the equipment rail from FIGS. 10 to 15.

FIG. 16 shows a further schematic view of the equipment rail 90 from FIGS. 10 to 15. The nature of the view, in particular the orientation of the drawing plane, corresponds to that of FIGS. 14 and 15. In FIG. 16, and as is also shown in FIG. 10, the cover cap 108 is turned over the plates 94, 104. In the position shown in FIGS. 10 and 16, the cover cap 108 can he held by locking lugs (not shown in the figures) or by other mechanisms. The cover cap 108 can be designed to generate a tactile and/or acoustic signal perceptible to humans when the position shown in FIGS. 10 and 16 is reached. The cover cap 108 holds the second plate 104 in the position shown in FIGS. 10, 15 and 16 relative to the first plate 94 and thus secures the form-fit connection between the two units of the equipment rail 90 and the locking of the connection between the equipment rail 90 and the column 30.

REFERENCE SIGNS 10 medical equipment carrier
20 base of the medical equipment carrier 10
21 roller unit on the base 20
22 vertical pivot axis of the roller unit 21 (steerability)
30 first column of the medical equipment carrier 10 (rear center)
37 channel on the first column 30 for arid bars 70
40 second column of the medical equipment carrier 10 (front left, right, arranged with mirror symmetry)
47 channel on the second column 40 for arid bars 70
60 bridge
70 grid bar on a first column 30 or on the second column 40
72 opening in the grid bar 70
73 web between two openings 72 in the grid bar 70
80 shelf (support device)
81 engagement hook on shelf 80
82 straight portion on the engagement hook 81
83 angled portion on the engagement hook 81
84 rivet for securing the engagement hook 81 on the support device 80
85 slide on the shelf 80
86 bolt on the slide 85 for locking the connection between engagement hook 81 and opening 72
87 locking lug on the slide 85
88 screw head on the engagement hook as mating piece for locking lug 87 on the slide 85
89 pin on the shelf 80 for engaging in opening 72
90 equipment rail (support device)
91 engagement hook on equipment rail 90
92 straight portion on the engagement hook 91
93 angled portion on the engagement hook 91
94 first plate on the engagement hook 91
95 bore in first plate 94
96 screw on first plate 94 for engaging in slit 107 on second plate 104
97 shank of the screw 96
98 head of the screw 96
100 spar
104 second plate at one end of the spar 100
105 axis about which the spar 100 and the second plate 104 are pivotable
106 pin (bolt) on the second plate 104 for locking the connection between engagement hook 91 and opening 72
107 slit in second plate 104 for receiving the screw 96 on first plate 94
108 cover cap for holding the spar 100 and the second plate 104 in the stable position

The invention claimed is:

1. A support device for releasable connection to an equipment carrier, and for supporting a medical appliance, comprising
   an engagement hook for engaging in an opening on a surface of the equipment carrier and
   a bolt for locking a connection between the engagement hook and the opening in which the engagement hook engages,
   wherein the engagement hook comprises a straight portion for engaging in the opening, and a portion which is angled in relation to the straight portion and is for engaging behind the opening, and the bolt is movable in the opening between an unlocking position and a locking position.

2. The support device according to claim 1, wherein, in the unlocking position, the bolt is not arranged next to the straight portion of the engagement hook and, in the locking position, the bolt is arranged next to the straight portion of the engagement hook.

3. The support device according to claim 1, wherein, in the unlocking position, the bolt does not engage in the opening on the equipment carrier in which the engagement hook engages, and, in the locking position, the bolt does engage in the opening on the equipment carrier in which the engagement hook engages.

4. The support device according to claim 1, wherein the bolt is held in the locking position.

5. The support device according to claim 4, wherein the bolt is held locked in the locking position.

6. The support device according to claim 4, wherein either a tactile signal or an acoustically perceptible signal is generated when the bolt is moved to the locking position.

7. The support device according to claim 1, further comprising a spar for supporting a medical appliance or a medical instrument or another payload, wherein the spar is connectable to the engagement hook, wherein the bolt is rigidly connected to the spar, wherein the bolt, in the locking position, engages through a bore on the engagement hook, wherein, in the locking position of the bolt, the spar is pivotable between a loose position and a stable position about an axis extending through the bolt, wherein, in the loose position of the spar, the bolt is movable between the locking position and the unlocking position and the spar can be separated from the engagement hook, wherein, in the stable position of the spar, the spar is mechanically connected to the engagement hook and is loaded with the payload.

8. The support device according to claim 7, further comprising a first plate, which is rigidly connected to the engagement hook and has the bore, and a second plate, which is rigidly connected to the spar and to the bolt, wherein the first plate and the second plate are connected to each other with a form fit in the stable position.

9. The support device according to claim 8, further comprising a cover cap that can be turned over the first plate and the second plate in order to hold the second plate relative to the first plate in the stable position.

10. An equipment carrier for carrying a payload, with a supporting framework, and an opening on the supporting framework, wherein the opening receives the engagement hook on the support device of claim 1.

11. The equipment carrier according to claim 10, in which the opening is a plurality of openings provided on the supporting framework, wherein the engagement hook on the support device can engage alternately in one of the plurality of openings.

12. The equipment carrier according to claim 11, in which the supporting framework comprises several columns, wherein several of the plurality of openings are provided on each column, the respective openings comprise different markings that are provided on each column, and the openings which receive the engagement hooks of the support device, in an intended arrangement of the support device, have identical or corresponding markings.

13. The equipment carrier according to claim 10, wherein the supporting framework further comprises several columns, each column with an opening, wherein several engagement hooks are provided on the support device and engage simultaneously in a respective opening.

14. A support device for releasable connection to an equipment carrier, and for supporting a medical instrument, comprising
an engagement hook for engaging in an opening on the equipment carrier, and
a bolt for locking a connection between the engagement hook and the opening in which the engagement hook engages,
the engagement hook comprises a straight portion for engaging in the opening, and a portion which is angled in relation to the straight portion and is for engaging behind the opening, and the bolt is movable in the opening between an unlocking position and a locking position where the bolt extends through the opening;
wherein the bolt is part of a slide arranged on the engagement hook.

15. The support device according to claim 1, wherein the bolt is part of a slide arranged on the engagement hook, the slide movable along a length of the engagement hook between the unlocking position and the locking position.

16. The support device according to claim 1, further comprising a removable spar for supporting a payload,
the bolt affixed to the spar such that in the locking position the bolt connects with the engagement hook through a bore on the engagement hook, and in the unlocking position the spar can be separated from the engagement hook.

17. A support device for releasable connection to an equipment carrier, and for supporting a medical appliance, comprising
an engagement hook for engaging in an opening on the equipment carrier and
a bolt for locking a connection between the engagement hook and the opening in which the engagement hook engages,
a removable spar for supporting a payload, the bolt affixed to the spar such that in a locking position the bolt connects with the engagement hook through a bore on the engagement hook, and in an unlocking position the spar can be separated from the engagement hook,
wherein the engagement hook comprises a straight portion for engaging in the opening, and a portion which is angled in relation to the straight portion and is for engaging behind the opening, and the bolt is movable in the opening between the unlocking position and the locking position.

18. The support device according to claim 1, in which a plurality of openings are provided on the equipment carrier, wherein the engagement hook can engage alternately in one of the plurality of openings.

19. The support device according to claim 18, in which the equipment carrier comprises several columns, and several respective openings are provided on each column.

20. The support device according to claim 14, in which a supporting framework of the equipment carrier comprises several columns, and several respective openings are provided on each column, wherein the engagement hook can engage alternately in one of the several respective openings.

* * * * *